United States Patent
Sommermeyer et al.

(12) 
(10) Patent No.: US 6,284,140 B1
(45) Date of Patent: Sep. 4, 2001

(54) DIALYSIS SOLUTION FOR PERITONEAL DIALYSIS

(75) Inventors: Klaus Sommermeyer, Rosbach; Jutta Passlick-Deetjen, Giessen, both of (DE)

(73) Assignee: Fresenius AG, Bad Homburg (DE)

( * ) Notice: Subject to any disclaimer, the term of this patent is extended or adjusted under 35 U.S.C. 154(b) by 0 days.

(21) Appl. No.: 08/815,442

(22) Filed: Mar. 11, 1997

Related U.S. Application Data

(63) Continuation of application No. 08/389,683, filed on Feb. 16, 1995, now abandoned, which is a continuation of application No. 08/167,366, filed on Dec. 16, 1993, now abandoned.

(30) Foreign Application Priority Data

Dec. 18, 1992 (DE) ................................................ 42 42 926

(51) Int. Cl.$^7$ ............................. A61M 1/28; A61K 31/70; A61K 31/715
(52) U.S. Cl. ......................... 210/647; 210/646; 514/60; 514/929; 536/111; 604/29
(58) Field of Search ................................ 210/645, 646, 210/647, 542; 424/677, 678, 679, 680, 681, 722, 717; 435/2; 436/826; 514/60, 832, 929; 604/29; 252/1, 183.13, 183.16; 536/1.11, 111

(56) References Cited

U.S. PATENT DOCUMENTS

| | | | |
|---|---|---|---|
| 4,879,280 | * 11/1989 | Seyffart et al. | 514/53 |
| 5,218,108 | 6/1993 | Sommermeyer et al. | 536/111 |
| 5,436,232 | * 7/1995 | Forster et al. | 514/60 |

FOREIGN PATENT DOCUMENTS

| | | |
|---|---|---|
| 34 28 201 | 2/1986 | (DE) . |
| 41 23 000 | 1/1993 | (DE) . |
| 41 23 001 | 1/1993 | (DE) . |
| 0 170 275 | 2/1986 | (EP) . |
| 402 724 | 12/1990 | (EP) . |

OTHER PUBLICATIONS

Hawley's Condensed Chemical Dictionary, Lewis, Jr. (ed.), Twelfth Edition, Van Nostrand Reinhold Company, New York (1993), p. 1010.*

Hain, H. et al. "Utrafiltration and Absorption Characteristics of Hydroxyethyl Starch and Dextran During Long Divell Peritoneal Dialysis Exchanges in Rats", Adv. Perit. Dial. 5, (1989) 528–30: Midline AN 91255348. (Only Abstract is Provided).

Gretz et al., "HES As An Osmotic Agent For Continuous Ambulatory Peritoneal Dialysis Solutions", Nephron 1992; 61:120.

Cantor et al. (ed), Rote Liste 1989, Verzeichnis von Fertigarznelmitteln der Mitglieder des Bundesverbandes der Pharmazeutlischen Industrie e.V.; Herausgeber:Bundesverband der Pharmazeutischen Industrie e.V,; Aulendorf/Württ (No English Translation).

Fresnius, "Infusionstherapie und Klinische Ernahrung", Aug. 8, 1983. (No English Translation).

* cited by examiner

*Primary Examiner*—John Kim
(74) *Attorney, Agent, or Firm*—Selitto, Behr & Kim

(57) ABSTRACT

The present invention relates to dialysis solutions for peritoneal dialysis, containing hydroxyethyl starch as the osmotically-active substance, electrolytes and, optionally, conventional additives, where the hydroxyethyl starch has a molecular weight Mw in the range from 10,000 to 150,000, a substitution MS in the range from 0.10 to 0.40, a substitution DS in the range from 0.09 to 0.35 and a substitution ratio C2/C6≧8. With this peritoneal dialysis solution it is possible, with an outstanding ultrafiltration, to maintain a longer dwell time, for example the dialysis solution can be utilized for a period of 12 hours in the CAPD without replacement. In addition, the inventive dialysis solution is also particularly advantageous for patients with residual kidney function. The resorption of the osmotically active substance is clearly diminished and even after a dwell time of 12 hours it amounts to a maximum of 60–70%.

23 Claims, No Drawings

DIALYSIS SOLUTION FOR PERITONEAL DIALYSIS

This is a continuation of application Ser. No. 08/389,683 filed Feb. 16, 1995, now abandoned, which is a continuation of application Ser. No. 08/167,366 filed on Dec. 16, 1993, abandoned, the disclosure of which in its entirety is incorporated herein by reference.

FIELD OF THE INVENTION

The present invention relates to dialysis solutions for peritoneal dialysis, containing hydroxyethyl starch as the osmotically-active substance, electrolytes and/or conventional additives.

DISCUSSION OF BACKGROUND INFORMATION

In solutions for peritoneal dialysis, for example continual ambulatory peritoneal dialysis (CAPD) or continual cycling peritoneal dialysis (CCPD) it is the usual practice to make use of glucose as the osmotic carrier substance or osmotic active substance. However, these solutions have the disadvantage that glucose when used as the carrier substance is strongly resorbed, because of which the glucose blood level is increased, which is very disadvantageous in the presence of disturbances of carbohydrate metabolism. Dialysis solutions for peritoneal dialysis, e.g. the continuous ambulant peritoneal dialysis (CAPD) or the continuous cycling peritoneal dialysis (CCPD) are disclosed in (cf. "Praxis der CAPD", published by F. Scheler and C. Fuchs, Bibliomed, Medizinische Verlagsgesellschaft mbH Melsungen, 1981, p. 1–139).

For this reason attempts have been made over long periods of time to replace the glucose in dialysis solutions for peritoneal dialysis with other substances which do not possess the disadvantages occurring when glucose is used as the osmotic active substance, that is to say, with which there is no undesirable resorption, and with which it is also possible to have longer dwell times and, therefore, a change is only necessary after longer intervals of time. A restricted choice of replacements for glucose can be made from poly-anionic substances and glycerin. However, poly-anionic substances have the disadvantage that they can cause alteration in the size of the membrane pores, thus having a negative influence on the dialysis. Studies with poly-anionic substances have not yet progressed beyond the stage of animal experiments. Also, substantial doubts exist about the utilisation of glycerin, because glycerin has a nephrotoxic effect and, since it can be resorbed because of its low molecular weight, it can disturb the residual kidney function.

According to the DE-OS 34 28 201, an hydroxyethyl starch with a molecular weight $\geq 3 \times 10^4$ Dalton and a degree of substitution in the range from 0.25 to 0.7 is proposed as the osmotic active substance in solutions for peritoneal dialysis.

However, the utilisation of such an hydroxyethyl starch, with regard to the problems of poor metabolisation of eventually absorbed hydroxyethyl starch, is unfavourable.

Hydroxyethyl starches are known from EP-A-0 402 724, which have a mean molecular weight in the range from 60,000 to 600,000, a degree of substitution MS and DS in the range from 0.15 to 0.5 and a substitution ratio C2/C6 in the range from 8 to 20. However, only the use of plasma expanders is described and no reference is made to the utilisation of hydroxyethyl starch in peritoneal dialysis.

However, from investigation, referred to in Nephron 1992, 61, 120 and in which the breakdown of hydroxyethyl starches of different molecular weights in various organs was compared, it can be gleaned that hydroxyethyl starches do not appear to be suitable for use as osmotically active substances in continuous ambulatory peritoneal dialysis.

Therefore, there still exists, as formerly, the need for dialysis solutions which contain osmotically active substances and with which the disadvantages of the known solutions do not occur.

SUMMARY OF THE INVENTION

The objective of the present invention is therefore the preparation of dialysis solutions for peritoneal dialysis which do not exhibit the disadvantages of known dialysis solutions, but which contain an osmotically active substance which is only slightly resorbed or scarcely at all, is readily metabolised, has no harmful effect for the peritoneum and possesses good osmotic activity.

DETAILED DESCRIPTION

Very surprisingly, it has been found that dialysis solutions which are characterised by the fact that they contain an hydroxyethyl starch having a molecular weight Mw in the range from 10,000 to 150,000, a degree of substitution MS in the range from 0.10 to 0.40, a degree of substitution DS in the range from 0.09 to 0.35 and a substitution ratio C2/C6$\geq$8, do not display the disadvantages of the known dialysis solutions.

The hydroxyethyl starch utilised in the inventive dialysis solutions preferably has a molecular weight Mw in the range from 10,000 to 55,000, in particular from 20,000 to 29,000, for example 29,000. The degree of substitution MS of the hydroxyethyl starch is preferably in the range from 0.10 to 0.24, in particular from 0.20 to 0.24, for example 0.23. The degree of substitution DS of the hydroxyethyl starch used is preferably in the range from 0.09 to 0.23, whilst the ratio C2/C6 of the starch utilised is preferably in the range from 8 to 25.

For purposes of the present invention as disclosed herein, the weight average of the molecular weights of hydroxyethyl starch was measured with MALLS-or LALLS-high pressure GPC (HPGPC, high pressure size exclusion chromatography).

Conditions of separation:

Stationary phase:
  Precolumn
  Spherogel TSK PWHR (4 cm×6 mm)
  Separation columns
  2×Spherogel TSK GMPWHR (30 cm×7.8 mm)
  Temperature 30° C.

Mobile phase:
  Acetate-buffer
  18.7 g sodium-acetate 3 $H_2O$ and 1,72 g sodium-azide dissolved in approximately 4 l $H_2O$ (bidest.) adding 34.5 ml acetic acid and filling it with $H_2O$ (bidest.) up to 5 l.

Flow rate:
  0,5 ml/min.
  a flow rate of 0.5 ml/min means that 0.5 ml acetate buffer passes within 1 minute through a Precolumn (4 cm×6 mm) and two Spherogel TSK GMPWHR (30 cm×7.8 mm) columns.

The production of the inventive hydroxyethyl starch utilised is effected in the manner known per se by hydrolytic and/or enzymatic degradation of a starch, in particular a starch rich in amylopectin, to a specified molecular weight and partial etherification to the desired degree of substitution. For production of the dialysis solution, a solid hydroxyethyl starch obtained for example by spray drying or vacuum drying can be utilised, or else the hydrolysis solutions obtained by purification, in particular by diafiltration, can be utilised.

An example of a process for preparing an hydroxyethyl starch is disclosed in U.S. Pat. No. 5,218,108, SOMMER-MEYER et al., the disclosure of which in its entirety is incorporated by reference thereto herein. As used herein, unless otherwise disclosed, the terms molecular weight, average molecular weight, mean molecular weight, substitution degree MS (molar substitution), substitution degree DS (degree of substitution), and the ratio of substitution of $C_2$ to the substitution of $C_6$ (the ratio $C_2/C_6$) have the same meaning as disclosed in U.S. Pat. No. 5,218,108.

The dialysis solution in accordance with the present invention contains the hydroxyethyl starch, preferably in an amount in the range from 3 to 10 percent by weight, based on the final solution.

The medium for the dialysis solution can be, for example, one used for peritoneal dialysis, in particular the conventional medium for peritoneal dialysis with glucose as the osmotically active carrier substance, for example Ringer's solution.

As used herein, a "Ringers Solution" includes sodium-, potassium-, calcium-, and chloride-ions, as disclosed in a) CANTOR (ed), *ROTE LISTE* 1989, Verzeichnis von Fertigarznelmitteln der Mitglieder des Bundesverbandes des Pharmazeutlischen Industrie e.V.; Herausgeber: Bundesvverband der Pharmazeutischen Industrie e.V.; Aulendorf/ Wurtt; and b) Fresnius, "Infusionstherapie und Klinische Ernahrung", Aug. 8, 1993. An example of a conventional Ringers solution, is disclosed in *Hawley's Condensed Chemical Dictionary,* LEWIS, Jr. (ed), Twelfth Edition, Van Nostrand Reinhold Company, New York, 1993, page 1010.

Along with hydroxyethyl starch as the osmotically active substance, the inventive solutions for peritoneal dialysis may contain additional substances, in particular those conventional ingredients for dialysis solutions such as, for example, the components of Ringer's solution. A preferred inventive dialysis solutions contains, for example, from 3 to 10 percent by weight of hydroxyethyl starch, 125 to 150 mMol/liter of sodium ions, 90 to 115 mMol/liter of chloride ions, 0.3 to 1.5 mMol/liter of magnesium ions, 1.0 to 2.5 mMol/liter of calcium ions and 30 to 45 mMol/liter of lactate. The lactate may be partly or totally replaced by acetate and/or bicarbonate. The named cations and anions are preferably salts of the components also named as counter-ions. However, other physiologically compatible cations and ions may be used, especially if there is an inadequate quantity of counter-ions.

The inventive dialysis solutions may also contain one or more pharmacologically active substances, such as those already used in conventional dialysis solutions. These active substances are, in particular, vasodilators such as sodium nitroprusside, diuretics, hormones such as insulin, and/or vitamins such as, in particular, Vitamin E. The nature and amounts of these active substances are, in particular, determined to suit the existing individual circumstances.

Glucose, preferably in an amount from 0.1 to 4.5 percent by weight, based upon the final solution, may be used as an additional component in the inventive dialysis solution. Addition of glucose is especially expedient if it also intended to supply a certain amount of nutrition with the dialysis solution.

The amounts of the components present along with the hydroxyethyl starch are, in particular, dependent upon the content of hydroxyethyl starch, in which case the nature and amounts of the pharmacologically active substances are, in particular, determined to suit the existing individual circumstances.

The inventive dialysis solution possesses a low osmolarity and is preferably iso-osmolar, or isotonic. For purposes of the present invention as disclosed herein osmolarity may be determined by weighing the amount of the compound that is dissolved in an isotonic solution.

The inventive dialysis solutions can be prepared in the manner known per se by dissolving the ingredients in distilled water, filtering the solution obtained, followed by sterilisation of the solution. The ingredients may all be added and dissolved together at the same time, but they may be added in such a manner that one or more ingredients are added and dissolved sequentially. For example, the hydroxyethyl starch and, optionally, other ingredients may be dissolved in a ready-prepared Ringer's solution or in any other medium suitable for this type of dialysis solution.

The dialysis solution is stored in containers commonly employed for peritoneal dialysis and used directly from them. These containers may be fabricated from solid materials (for example, glass) or else from a flexible material (for example, synthetic plastics material) and, in particular, from thin sheets of synthetic plastics material so that they may be folded up.

It is preferable to carry out the production and/or sterilisation of the dialysis solutions in containers suitable for their storage and Subsequent utilisation. In many respects (storage, transport, stability of the solution, selection of the dialysis solution for a particular purpose) it may also be expedient, for some or all of the ingredients of the dialysis solution in the solid state, for example in lyophilized form, to be filled into the dialysis container and for them to be dissolved, shortly before their utilisation, in a suitable medium, for example in distilled water or Ringer's solution.

The inventive dialysis solutions, when compared with the known dialysis solutions which contain glucose as the osmotically active substance, make it possible for them to be used for longer periods of time, that is to say, the dwell time between replacements is increased. Thus, for example, it is possible when using the inventive dialysis solutions, to carry on the CAPD for a period of 12 hours (without replacement). The inventive dialysis solution is also particularly advantageous for patients with residual kidney function. The resorption of the osmotically active substance is clearly diminished by the invention. In addition to this, there is the further advantage that the hydroxyethyl starch utilised in accordance with the present invention is easily degraded and is non-toxic.

EXAMPLES

The following examples will serve to explain the invention.

Example 1

By utilisation of the ingredients listed below, a dialysis solution in accordance with the present invention is produced. (Amounts/1000 ml):

| | |
|---|---:|
| Hydroxyethyl starch | 75.0 g |
| Mw 29,000 | |
| MS 0.23 | |

-continued

| | |
|---|---|
| DS 0.21 | |
| C2/C6 8.7 | |
| Sodium chloride | 5.435 g |
| Sodium L-lactate (50% solution) | 8.97 g |
| Calcium chloride dihydrate | 0.2573 g |
| Magnesium chloride hexahydrate | 0.0508 g |
| Water for injections | 945 ml |

The preparation of the inventive dialysis solution is effected as follows:

The stated amount of sodium chloride, the sodium L-lactate (50% solution), the calcium chloride, the magnesium chloride and the hydroxyethyl starch were added to 945 ml of water for injections in that order and dissolved with stirring. When solution was complete, 0.25 g of activated charcoal (DAB 9) was added and, after stirring for 20 minutes, the mixture was filtered through a Seitz filter Supra EK 1P and subsequently through an 0.2 micron membrane filter into the cooling tank. The pH value was adjusted to be in the range 5.8 to 5.9, by the addition of either 25% hydrochloric acid or sodium hydroxide solution. The solution obtained was subsequently filtered through a membrane pre-filter and then through an 0.2 micron membrane filter. The filtered solution was then filled into suitable containers and, after sealing the containers, was sterilised.

Sterilisation: at 121° C. for 15 minutes with additional time for equilibration.

The solution obtained had the following characteristics:

| | |
|---|---|
| pH-value | 5.0 to 6.0 |
| Density: | 1.032 to 1.038 |
| Osmolarity | 2.72 mosmol/liter |
| Titration acidity: | 0.3–2.0 mMol NaOH/liter. |

Example 2

The dialysis solutions prepared according to Example 1 was tested with respect to its effectiveness as a dialysis solution.

For purposes of comparison, a dialysis solution was utilised which was prepared in a similar manner to the dialysis solution prepared according to Example 1 and it had the same composition with the exception that, instead of the hydroxyethyl starch used in Example 1, 42.5 g of glucose was used.

The investigations were carried out in the conventional manner, in which case the experimental animals were uraemic rabbits (5/6 nephrectomised).

In the group investigated, in which the effectiveness of hydroxyethyl starch (HES) was test, six animals were used and, in the group in which glucose was used as the osmotically active substance, eight animals were used. In these investigations, ultrafiltration was carried out at 2 hours, 4 hours, 6 hours and 12 hours respectively and the percentage retrieval of the relevant osmotically active substance (i.e., hydroxyethyl starch or glucose) was determined in the dialysate outflow.

The results show that hydroxyethyl starch, when compared with glucose, gives outstanding ultrafiltration even over a period of 12 hours. Furthermore, it may be seen from the results obtained with the utilisation of hydroxyethyl starch, that only relatively slight resorption occurs, and over a period of 12 hours a resorption of only 60–70% occurred, whereas with the utilisation of glucose, the glucose was resorbed to a considerable degree after a relatively short time and, after a period of 12 hours, the whole of the glucose was resorbed.

The results obtained from the investigations are set out in the Tables A to D.

TABLE A

Ultrafiltration (ml)
HES (Therapy phase)

| Duration | Animal 1 | Animal 2 | Animal 3 |
|---|---|---|---|
| 2 h | 30 | 20 | 20 |
| 4 h | 100 | 55 | 75 |
| 6 h | 200 | 80 | 95 |
| 12 h | 100 | 175 | 105 |

| Duration | Animal 4 | Animal 5 | Animal 6 |
|---|---|---|---|
| 2 h | 130 | 125 | 50 |
| 4 h | 60 | 130 | 105 |
| 6 h | 120 | 145 | 135 |
| 12 h | 140 | 180 | 210 |

TABLE B

Ultrafiltration (ml)
Glucose 4.25% (Therapy phase)

| Duration | Animal 1 | Animal 2 | Animal 3 | Animal 4 |
|---|---|---|---|---|
| 2 h | 100 | 105 | 125 | 55 |
| 4 h | | 100 | 100 | 140 |
| 6 h | 40 | 70 | 70 | 35 |
| 12 h | −130 | −80 | −50 | −85 |

| Duration | Animal 5 | Animal 6 | Animal 7 | Animal 8 |
|---|---|---|---|---|
| 2 h | −5 | 90 | 85 | 90 |
| 4 h | −60 | 60 | 55 | 75 |
| 6 h | −45 | −40 | 35 | 0 |
| 12 h | −160 | −200 | −125 | −150 |

TABLE C

Percentage retrieval in dialysate outflow
HES

| Duration | Animal 1 | Animal 2 |
|---|---|---|
| 2 h | 65.6 | 61.5 |
| 4 h | 64.6 | 57.0 |
| 6 h | 70.4 | 41.0 |
| 12 h | 23.3 | 39.3 |

| Duration | Animal 4 | Animal 5 | Animal 6 |
|---|---|---|---|
| 2 h | 73.4 | 42.6 | 74.4 |
| 4 h | 47.7 | 66.2 | 68.7 |
| 6 h | 51.6 | 54.1 | 66.5 |
| 12 h | 38.4 | 38.5 | 48.0 |

TABLE D

Percentage Retrieval in Dialysate Outflow

When glucose (4.25%) was used, all the values found were less than 10%.

Example 3

Example 1 was repeated with the exception that, instead of the hydroxyethyl starch used there, 75 g of an hydroxyethyl starch with the following characteristics was used:

| Mw | 130,000 |
|---|---|
| MS | 0.4 |
| DS | 0.35 |
| C2/C6 | 9 |

What is claimed is:

1. A method for peritoneal dialysis comprising treating a subject with a peritoneal dialysis solution comprising at least one member selected from the group consisting of electrolytes and additives, and hydroxyethyl starch, wherein said hydroxyethyl starch comprises an average molecular weight in a range from 10,000 to 150,000, a molar substitution in a range from 0.10 to 0.40, a degree of substitution in a range from 0.09 to 0.35, and a substitution ratio C2/C6 in a range from 8 to 25, and wherein said hydroxyethyl starch is present in said peritoneal dialysis solution in an effective amount for peritoneal dialysis.

2. The method according to claim 1, wherein said hydroxyethyl starch comprises an average molecular weight in the range from 10,000 to 55,000.

3. The method according to claim 2, wherein said hydroxyethyl starch comprises an average molecular weight in the range from 20,000 to 29,000.

4. The method according to claim 1, wherein said molar substitution of said hydroxyethyl starch comprises a value in the range from 0.10 to 0.24.

5. The method according to claim 4, wherein said molar substitution of said hydroxyethyl starch comprises a value in the range from 0.20 to 0.24.

6. The method according to claim 1, wherein said degree of substitution of said hydroxyethyl starch comprises a value in the range from 0.09 to 0.23.

7. The method according to claim 1, wherein said effective amount of said hydroxyethyl starch is a concentration in a range from 3 to 10 percent by weight, based on said peritoneal dialysis solution.

8. The method according to claim 1, wherein said peritoneal dialysis solution comprises an effective amount within a range from 3 to 10 percent by weight of hydroxyethyl starch, 125 to 150 mMol/liter of sodium ions, 90 to 115 mMol/liter of chloride ions, 0.3 to 1.5 mMol/liter of magnesium ions, 1.0 to 2.5 mMol/liter of calcium ions and 30 to 45 mMol/liter of salts selected from the group consisting of lactate, acetate, and bicarbonate.

9. The method according to claim 8, wherein said peritoneal dialysis solution further comprises from 0.1 to 4.25 percent by weight of glucose, based on said peritoneal dialysis solution.

10. The method according to claim 1, wherein said electrolytes are selected from the group consisting of chlorides, lactates, acetates, and bicarbonates.

11. The method according to claim 1, wherein said additives are selected from the group consisting of pharmacologically active substances suitable for dialysis solutions.

12. The method according to claim 11, wherein said pharmacologically active substances are selected from the group consisting of vasodilators, diuretics, hormones, and vitamins.

13. A dialysis solution for peritoneal dialysis comprising hydroxyethyl starch, and at least one member selected from the group consisting of electrolytes and additives, wherein said hydroxyethyl starch comprises an average molecular weight in a range from 10,000 to 55,000, a molar substitution in a range from 0.10 to 0.40, a degree of substitution in a range from 0.09 to 0.35 and a substitution ratio C2/C6 in a range from 8 to 25.

14. The dialysis solution according to claim 11, wherein said hydroxyethyl starch comprises an average molecular weight in the range from about 20,000 to 29,000.

15. The dialysis solution according to claim 14, wherein said molar substitution of the said hydroxyethyl starch comprises a value in the range from 0.10 to 0.24.

16. The dialysis solution according to claim 15, wherein said molar substitution of said hydroxyethyl starch comprises a value in the range from 0.20 to 0.24.

17. The dialysis solution according to claim 16, wherein said degree of substitution of said hydroxyethyl starch comprises a value in the range from 0.09 to 0.23.

18. The dialysis solution according to claim 16, wherein said hydroxyethyl starch is present in a concentration in the range from 3 to 10 percent.

19. The dialysis solution according to claim 18, wherein said dialysis solution comprises from 3 to 10 percent by weight of hydroxyethyl starch, 125 to 150 mMol/liter of sodium ions, 90 to 115 mMol/litre of chloride ions, 0.3 to 1.5 mMol/liter of magnesium ions, 1.0 to 2.5 mMol liter of calcium ions, and 30 to 45 mMol/liter of a salt selected from the group consisting of lactate, acetate, and bicarbonate.

20. The dialysis solution according to claim 19, wherein said dialysis solution, further comprises from 0.1 to 4.25 percent by weight of glucose, based on said peritoneal dialysis solution.

21. The dialysis solution according to claim 13, wherein said electrolytes are selected from the group consisting of chlorides, lactates, acetates, and bicarbonates.

22. The dialysis solution according to claim 13, wherein said additives are selected from the group consisting of pharmacologically active substances suitable for dialysis solutions.

23. The dialysis solution according to claim 13, wherein said pharmacologically active substances are selected from the group consisting of vasodilators, diuretics, hormones, and vitamins.

* * * * *